United States Patent
Rudholzer et al.

(10) Patent No.: US 8,870,569 B2
(45) Date of Patent: Oct. 28, 2014

(54) MEDICAL OR DENTAL HANDPIECE HAVING A BEARING ARRANGEMENT FOR A ROTARY PART

(75) Inventors: Andreas Rudholzer, Nussdorf (AT); Stefan Rusch, Pantaleon (AT); Gernot Ploy, Bürmoos (AT); Gerhard Hochradi, Pantaleon (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 987 days.

(21) Appl. No.: 12/629,726

(22) Filed: Dec. 2, 2009

(65) Prior Publication Data

US 2010/0136503 A1    Jun. 3, 2010

(30) Foreign Application Priority Data

Dec. 2, 2008   (EP) .................................. 08020869

(51) Int. Cl.
 *A61C 1/10*  (2006.01)
 *A61C 1/18*  (2006.01)
 *F16C 33/58* (2006.01)

(52) U.S. Cl.
CPC ............. *A61C 1/181* (2013.01); *F16C 2316/13* (2013.01); *F16C 33/58* (2013.01)
USPC .......................................... 433/114

(58) Field of Classification Search
USPC .................................... 433/103–133
See application file for complete search history.

(56) References Cited

U.S. PATENT DOCUMENTS

| | | | | |
|---|---|---|---|---|
| 5,054,149 A * | 10/1991 | Si-Hoe et al. | ...................... | 15/28 |
| 7,667,361 B2 * | 2/2010 | Nobe et al. | ...................... | 310/90 |
| 2004/0161723 A1 * | 8/2004 | Helfenbein | ...................... | 433/132 |
| 2009/0023108 A1 * | 1/2009 | Novak et al. | ................... | 433/131 |
| 2009/0274992 A1 * | 11/2009 | Kim | ............................. | 433/132 |

FOREIGN PATENT DOCUMENTS

| | | |
|---|---|---|
| DE | 466 388 | 10/1928 |
| EP | 0 958 791 | 11/1999 |

OTHER PUBLICATIONS

European Search Report for EP08020869 (mailed May 27, 2009).

\* cited by examiner

*Primary Examiner* — Sunil K Singh
(74) *Attorney, Agent, or Firm* — Klarquist Sparkman, LLP

(57) ABSTRACT

The medical or dental handpiece comprises a rotary part and at least one roller bearing which is provided for bearing support of the rotary part. The roller bearing has a bearing inner ring and a bearing outer ring, each having a raceway for the at least one rolling element arranged therebetween. The rotary part is mounted on at least one bearing ring on the side having the raceway for the at least one rolling element.

17 Claims, 2 Drawing Sheets

MEDICAL OR DENTAL HANDPIECE HAVING A BEARING ARRANGEMENT FOR A ROTARY PART

CROSS REFERENCE TO RELATED APPLICATION

The present application claims priority from pending European Patent Application No. 08020869 filed Dec. 2, 2008, which is incorporated herein by reference.

BACKGROUND

1. Field

This application relates to the field of medical handpieces, which include dental handpieces, and in particular to a bearing arrangement for a rotary part of the handpiece.

2. Description of Prior Art

Such medical or dental handpieces serve to drive medical or dental tools using a drive mechanism that has at least one rotary part pivotably (or rotatably) mounted by a bearing arrangement. This part may be, e.g., a tool holder for receiving the tool. In the case of a mechanical drive, it may be a pivotably mounted shaft or in the case of a compressed gas operated turbine drive, it may preferably be a rotor arranged in the head. Medical and dental handpieces may thus have rotary parts pivotably mounted in various areas.

The bearing configuration of the rotary part is formed with at least one bearing which allows rotation of the rotary part with respect to the handpiece. A roller bearing having at least one rolling element arranged between a bearing inner ring and a bearing outer ring is preferably used. The bearing inner ring and bearing outer ring thus each form a raceway for the at least one rolling element.

The tool provided for treatment may be, for example, a rotary tool such as a drill or a tool movable back and forth, e.g., a file for preparation of a root canal.

Such a conventional medical or dental handpiece having a bearing arrangement for a rotary part is known from EP 0 958 791 B1.

Such bearing arrangements known in the prior art for medical or dental handpieces have a rotary part, preferably a bushing for a chucking system or a rotating shaft and at least one roller bearing, preferably a ball bearing. The at least one bearing has a bearing inner ring, a bearing outer ring and at least one rolling element. The at least one roller bearing supports the rotary part to allow it to rotate with respect to the handpiece by the bearing inner ring and the bearing outer ring. The at least one rolling element is supported between the bearing outer ring and an outer side of the bearing inner ring. The inner side of the bearing inner ring supports the rotary part.

One disadvantage of this conventional configuration of the bearing for the rotary part has proven to be the outside diameter of the bearing arrangement, which is determined on the basis of the bearing of the rotary part on the inside of the bearing inner ring. This is determined by the diameter of the several components, namely the rotary part, the bearing inner ring, the at least one rolling element and the bearing outer ring.

Another disadvantage of the conventional configuration is due to the assembly of the bearing part to be supported in the bearing inner ring of the at least one roller bearing. In the prior art, it is common to assemble such roller bearings by pressing them onto the rotary part. However, this assembly results in a negative effect on the roller bearing. By pressing the bearing inner ring onto the rotary part, the roller bearing structure, in particular the desired play of the at least one rolling element with respect to its raceways on the bearing inner ring and on the bearing outer ring, is influenced in a negative manner. Pressing the bearing inner ring onto the rotary part causes the bearing inner ring to widen in the area of the raceways of the at least one rolling element. This leads to a change in the adjustment between the at least one rolling element and its raceways on the bearing rings and thus to an unwanted shortening of the lifetime of the roller bearings.

SUMMARY

Described below are new approaches for a bearing arrangement for a rotary part of a medical or dental handpiece that avoid these and other disadvantages of the prior art while being simple to manufacture and facilitating in particular bearing of the rotary parts easily and in a space-saving manner.

According to one exemplary embodiment for supporting a rotary part in a medical or dental handpiece having a rotary part and at least one roller bearing which is provided for support of the rotary part and which has a bearing inner ring and a bearing outer ring, each with at least one raceway for the at least one rolling element arranged in between, the rotary part is supported on at least one bearing ring on the side having the raceway for the at least one rolling element.

For the bearing of the rotary part, preferably on the bearing inner ring on the side having the raceway for the at least one rolling element, it also has a contact surface for the rotary part, in addition to the raceway for the at least one rolling element. The application of an additional contact surface in addition to the raceway of the at least one rolling element typically requires an increase in the overall height of the bearing ring. This bearing ring, whether it is the bearing outer ring or the bearing inner ring, thus typically has a greater overall height than the bearing inner ring or bearing outer ring, respectfully, of that bearing.

The rotary part to be supported, which may be in particular a tool holder that serves to receive a tool, in particular a hollow shaft, a pivotably mounted shaft or a rotor arranged in the head, it is designed to receive the bearing inner ring, preferably with an opening. The bearing inner ring is thus mounted in the opening of the hollow rotary part on the side having the raceway for the at least one rolling element.

The present bearing arrangement for a rotary part is characterized by a number of substantial advantages.

The bearing of the rotary part on at least one roller bearing on one of the bearing rings, preferably on the bearing inner ring on the side having the raceway for the at least one roller element, allows a reduction in the diameter of the bearing arrangement. This is advantageous because the diameter of the bearing arrangement is determined only by the dimensions of the roller bearing, namely by the diameter of the bearing inner ring, of the roller element, and of the bearing outer ring, and not, as is required in the conventional configuration, by the diameter of the rotary part and additionally by the roller bearing design.

Assembling the rotary part on the bearing ring having the contact surface yields another advantage of the present bearing arrangement. Specifically, the present bearing arrangement can be assembled by conventional pressing, such that the rotary part is now pressed next to the raceways of the at least one rolling element against one of the bearing rings. Therefore, this assembly does not result in any impairment of the adjustment between the at least one rolling element and its raceways on the bearing rings.

In addition, the present bearing arrangement, besides minimizing the outside diameter of the bearing structure, makes it possible to retain the inside diameter of the rotary part that is used, by applying an offset in the opening of the rotary part for supporting the bearing ring which is lengthened and has the contact surface. When using a tool holder with a chucking bushing as the rotary part, the bearing ring additionally serves as a tool guidance surface or structure, which is advantageous.

In addition, with the present bearing arrangement, if using a chucking sleeve as the rotary part, it is possible to transfer torque to the tool that is to be chucked with the bearing inner ring. The bearing ring can therefore is therefore provided with a polygon and the tool is provided with a complementing recess. This recess is preferably designed as a polygon, in particular as a hexagon.

Within the scope of this application, it is self-evident that the bearing arrangement is not limited to the rotary parts mentioned in the description but instead additional rotary parts, e.g., motor shafts of motor-operated handheld pieces, may be pivotably mounted by the present bearing arrangement.

These and other embodiments are described in greater detail below on the basis of an exemplary embodiment in conjunction with the accompanying drawings.

DETAILED DESCRIPTION

Figure 1:
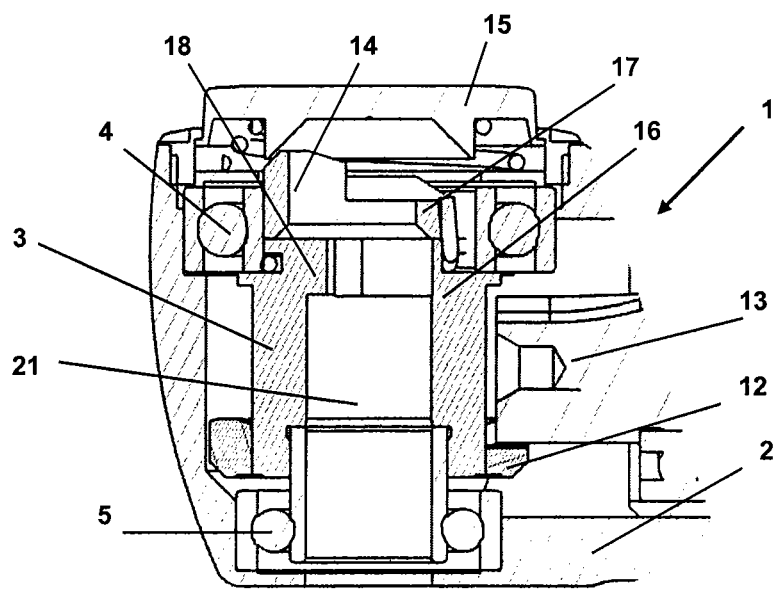
FIG. 1 shows a longitudinal section through the head area of a medical or dental handpiece with a tool holder as the rotary part to be supported.

FIG. 1 shows the head area of a medical or dental handpiece 1 having a head housing 2 and a pushbutton 15. A rotary part 3 having a passage or opening 21 and two roller bearings 4, 5 provided for bearing support of the rotary part 3 are accommodated in the head housing 2. The rotary part 3 here is designed as a tool holder and has a chucking sleeve 16 and a chucking member 14 with a locking body 17 and an entraining element 18 for transfer of torque. In addition, a crown wheel 12 is illustrated, serving to transfer the rotational motion from the shaft 13 to the rotary part 3.

Figure 2:
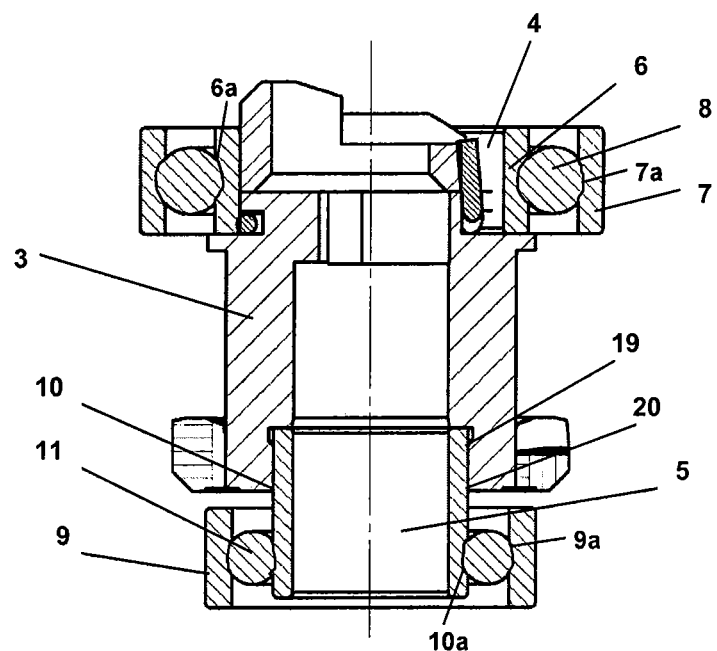
FIG. 2 shows a longitudinal section of the tool holder from FIG. 1 in the unassembled state.

The rotary part 3 shown in FIG. 2 is formed by the tool holder shown in FIG. 1 in the uninstalled state. The bearing support of the rotary part 3 is accomplished by two roller bearings 4, 5, each of which has its own bearing inner ring 6, 10, respectively, and its own bearing outer ring 7, 9, respectively. At least one rolling element 8 is provided between the bearing rings 6, 7 within respective raceways 6a, 7a. Similarly, at least one rolling element 11 is provided between the bearing rings 9, 10 within respective raceways 9a, 10a.

The rotary part 3 is supported on at least one roller bearing 5 on a bearing ring 9, 10 on the side having the raceway for the at least one rolling element 11. In addition to a raceway for the at least one rolling element 11, the illustrated bearing inner ring 10 has an extended portion with a contact surface 20 to receive the rotary part 3 to support the rotary part or to be connected thereto so that it is rotatable with respect to the handpiece. Therefore, the bearing inner ring 10 has a greater overall height than the bearing outer ring 9, which belongs to the roller bearing. To retain the inside diameter of the rotary part 3, in addition to minimizing the outside diameter of the bearing arrangement, it is advantageous to provide an offset 19 in an opening 21 on the rotary part 3. The inside diameter of the rotary part 3 may thus be retained due to the accommodation of the lengthened bearing inner ring 10 having the contact surface 20 in the offset 19. Consequently, when using the rotary part 3 as a chucking sleeve of a tool holder, the bearing inner ring 10 may be used as a tool guide for the tool to be chucked there on the side opposite the contact surface and the raceway for the at least one rolling element 11. In addition, for transfer of torque to the tool, entraining elements may be arranged on the side serving as the tool guide. To do so, the interior side of the bearing inner ring 10 may preferably be designed as a polygon, in particular as a hexagon.

Figure 3:
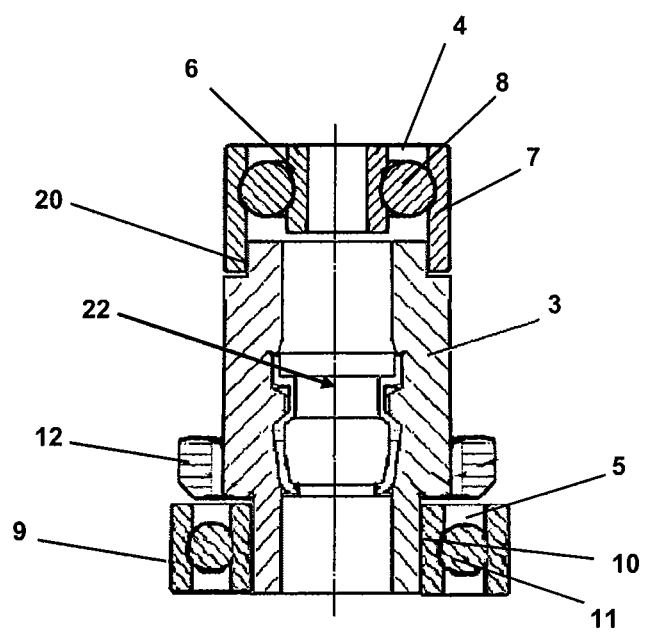
FIG. 3 shows a longitudinal section of the tool holder similar to FIG. 2, except with the bearing outer ring supporting the rotary part.

FIG. 3 illustrates an alternative configuration in which the outer ring 7 of the roller bearing 4 has an extended axial dimension or height, thereby defining the contact surface 20 along at least a portion of its inner surface. It is this inner surface of the outer ring 7 that also has a raceway defined therein for the rolling element 8.

As shown in FIG. 3, an upper end of the rotary part 3 can be shaped to engage with the contact surface 20 so that the rotary part is supported by the roller bearing 4. Among other advantages, this configuration allows for maintaining at least a smaller outside diameter of the roller bearing 4.

As also shown in FIG. 3, the rotary part 3 can be provided with a chucking bracket 22 to allow chucking of a tool. As illustrated in FIG. 3, the chucking bracket 22 can be provided instead of the chucking arrangement shown in FIG. 1, but in some situations it may be possible to use both chucking arrangements.

The scope of the present application is not limited to the exemplary embodiments described herein, but is defined by the following claims. Within the scope of this application, it is self-evident that the bearing support of the rotary part may be accomplished using the outside surface of the bearing inner ring or the inside surface of the bearing outer ring.

What is claimed is:

1. Medical or dental handpiece comprising a rotary part and at least one roller bearing provided for bearing support of the rotary part, said roller bearing having a bearing inner ring with an outer surface having a first raceway defined therein and a bearing outer ring with an inner surface having a second raceway defined therein, further comprising at least one rolling element arranged between the first raceway and the second raceway, wherein the bearing inner ring extends axially beyond the outer ring, and wherein the outer surface of the inner ring has a contact surface defined at a position axially spaced from the first raceway and at which the inner ring contacts the rotary part.

2. Medical or dental handpiece according to claim 1, wherein the rotary part is designed as a shaft for transmitting drive motion in the handpiece.

3. Medical or dental handpiece according to claim 1, wherein the rotary part is designed as a tool holder which preferably comprises a hollow shaft.

4. Medical or dental handpiece according to claim 3, wherein the tool holder has a chucking sleeve and a chucking member.

5. Medical or dental handpiece according to claim 4, wherein the chucking member comprises at least one locking body, which engages in a groove on a side of the tool.

6. Medical or dental handpiece according to claim 4, wherein the tool holder comprises at least one of a crown wheel and a rotor for transmitting the drive motion.

7. Medical or dental handpiece according to claim 4, wherein the tool holder comprises at least one entraining element for transmitting torque to the tool.

8. Medical or dental handpiece according to claim 1, wherein the outer surface of the bearing inner ring has at least one entraining element for transmitting the torque on its opposite side.

9. Medical or dental handpiece according to claim 7, wherein the entraining element is designed for transmitting torque by a polygonal-shaped recess.

10. Medical of dental handpiece according to claim 9, wherein the polygonal-shaped recess is hexagonally-shaped.

11. Medical or dental handpiece according to claim 8, wherein the entraining element is designed for transmitting torque by a polygonal-shaped recess.

12. Medical of dental handpiece according to claim 11, wherein the polygonal-shaped recess is hexagonally-shaped.

13. Medical or dental handpiece according to claim 1, wherein the rotary part has an offset and the bearing inner ring is dimensioned to abut against the offset.

14. Method for manufacturing a device for bearing support of a rotary part, comprising:
  providing a rotary part,
  providing at least one roller bearing having a bearing inner ring with an outer surface having a first raceway, a bearing outer ring with an inner surface having a second raceway and at least one rolling element positioned between the first raceway and the second raceway, the bearing inner ring projecting axially beyond the outer ring and defining a contact surface axially spaced from the first raceway, and
  connecting the rotary part to the contact surface to support the rotary part on the outer surface of the bearing inner ring.

15. Method for manufacturing a device for bearing support of a rotary part according to claim 14, wherein the rotary part is connected to the inner bearing inner ring by pressing or welding.

16. Medical or dental handpiece according to claim 1, wherein the roller bearing is a first bearing, further comprising a second bearing having a second bearing inner ring with a third raceway, and wherein the rotary part is supported by the second bearing by contact between the rotary part and a side of the second bearing inner ring opposite the third raceway.

17. Method for manufacturing a device for bearing support of a rotary part according to claim 14, further comprising providing a second bearing and connecting the rotary part with the second bearing to rotatably support the rotary part, wherein the second bearing has a second bearing inner ring with an outer surface having a raceway and an opposite inner surface, and wherein the inner surface of the second inner ring contacts the rotary part.

\* \* \* \* \*